United States Patent [19]
Armstrong et al.

[11] Patent Number: 6,048,721
[45] Date of Patent: *Apr. 11, 2000

[54] BIOREACTOR FOR MAMMALIAN CELL GROWTH AND MAINTENANCE

[75] Inventors: R. Douglas Armstrong, Ann Arbor; James Maluta, Dexter, both of Mich.; David Roecker, Denver, Colo.

[73] Assignee: Aastrom Biosciences, Inc., Ann Arbor, Mich.

[*] Notice: This patent issued on a continued prosecution application filed under 37 CFR 1.53(d), and is subject to the twenty year patent term provisions of 35 U.S.C. 154(a)(2).

[21] Appl. No.: 08/939,489

[22] Filed: Sep. 29, 1997

Related U.S. Application Data

[63] Continuation of application No. 08/478,622, Jun. 7, 1995, Pat. No. 5,688,687.

[51] Int. Cl.$^7$ ............................................. C12M 3/00
[52] U.S. Cl. ............................ 435/286.5; 435/286.6; 435/287.2; 435/293.2
[58] Field of Search ........................... 435/293.2, 297.2, 435/297.5, 372, 373, 401, 286.1, 286.5, 286.6; 422/48; 210/321.75, 321.84

[56] References Cited

U.S. PATENT DOCUMENTS

| | | |
|---|---|---|
| 3,847,749 | 11/1974 | Smith et al. . |
| 3,964,467 | 6/1976 | Rose . |
| 4,064,006 | 12/1977 | Rose . |
| 4,189,470 | 2/1980 | Rose . |
| 4,508,819 | 4/1985 | Rose . |
| 4,618,586 | 10/1986 | Walker . |
| 4,654,308 | 3/1987 | Safi et al. ............................. 435/294.1 |
| 4,659,655 | 4/1987 | Rose . |
| 4,861,483 | 8/1989 | Efthymiou et al. . |
| 5,153,131 | 10/1992 | Wolf et al. ........................... 435/297.2 |
| 5,223,428 | 6/1993 | Rose . |
| 5,416,022 | 5/1995 | Amiot ................................... 435/297.2 |
| 5,424,209 | 6/1995 | Kearny . |
| 5,459,069 | 10/1995 | Palsson et al. ........................ 435/297.2 |
| 5,571,720 | 11/1996 | Grandics et al. . |
| 5,612,188 | 3/1997 | Shuler et al. . |
| 5,688,687 | 11/1997 | Palsson et al. ........................ 435/293.2 |
| 5,690,893 | 11/1997 | Ozawa et al. . |

FOREIGN PATENT DOCUMENTS

| | | |
|---|---|---|
| 0 112 155 | 6/1984 | European Pat. Off. . |
| 0 531 631 | 3/1993 | European Pat. Off. . |
| WO 90/15877 | 12/1990 | WIPO . |
| WO 92/11355 | 7/1992 | WIPO . |
| 93/18132 | 9/1993 | WIPO . |

OTHER PUBLICATIONS

Crouch et al. "The Adhesion of Animal Cells to Surfaces . . . " J. Chem. Tech. Biotech. vol. 35B (1985)pp. 273–281.

*Primary Examiner*—William H. Beisner
*Attorney, Agent, or Firm*—Oblon, Spivak, McClelland, Maier & Neustadt, P.C.

[57] ABSTRACT

A bioreactor for the ex vivo maintenance and growth of mammalian cells includes a disposable, self contained cell cassette, a system manager, an incubator unit matable with a plurality of the cassettes and a processor unit. The cell cassette includes a substantially circular cell growth chamber defined between a substantially planar cell bed and a gas permeable, liquid impervious membrane. A media inlet enters the cell growth chamber communicates at a radially central portion of the cell bed. A plurality of media outlets are radially outwardly spaced from the media inlet by a distance sufficient for cell growth to occur between the inlet and the outlets. The outlets are substantially equiangularly circumferentially spaced about the cell growth chamber.

17 Claims, 11 Drawing Sheets

BIOREACTOR FOR MAMMALIAN CELL GROWTH AND MAINTENANCE

This is a Continuation of application Ser. No. 08/478,622, filed on Jun. 7, 1995, now U.S. Pat. No. 5,688,687.

BACKGROUND OF THE INVENTION

1. Field of the Invention

The present invention is directed to a bioreactor for the ex vivo growth of normal mammalian cells, especially the maintenance and selective growth of human stem and/or hematopoietic cells.

2. Background of the Invention

There is a significant interest in the ability to use cells for a wide variety of therapeutic purposes. The hematopoietic system exemplifies an extraordinary range of cells involved in protection of mammalian hosts from pathogens, toxins, neoplastic cells and other diseases. The hematopoietic system is believed to evolve from a single stem cell, from which all the lineages of the hematopoietic derive. The hematopoietic cells are known to grow and mature to varying degrees in bone as part of the bone marrow. It therefore becomes of interest to recreate a system which provides substantially the same environment as is encountered in the bone marrow, as well as being able to direct the cells which are grown in culture to a specific lineage. This is described in greater detail in U.S. patent application Ser. No. 08/178,433 filed on Jan. 6, 1994, now U.S. Pat. No. 5,459,069, which is a continuation of U.S. patent application Ser. No. 07/845,969, filed on Mar. 4, 1992 and now abandoned, and which is a continuation in part of U.S. patent application Ser. No. 07/366,639, filed on Jun. 15, 1989, and now also abandoned. The above applications are herein incorporated by reference into the present application. Also here incorporated by reference is our new U.S. patent application entitled "APPARATUS AND METHOD FOR MAINTAINING AND GROWING BIOLOGICAL CELLS," filed on Jun. 7, 1995 by the firm of Schroeder, Brueggemann & Clark of Los Angeles, Calif., and having attorney docket no. P03 33674 U.S. patent application Ser. No. 08/483,520, now abandoned.

The particular manner in which human stem cells proliferate and differentiate into their lineage is not completely understood, nor are the factors defined. However, once a human stem cell has become dedicated to a particular lineage, there appear to be a number of factors, for example colony stimulating factors, which allow, and may direct, the stem cell to a particular mature cell lineage. These colony stimulating factors include the oxygen concentration, and the rate of flow of, and the concentration of nutrients and waste products in, a liquid growth medium within which the cell colony is perfused.

SUMMARY OF THE INVENTION

It is accordingly an object of the present invention to provide a bioreactor for the maintenance and proliferation of human cells, including human stem cells and/or early human hematopoietic cells, including complex primary cell cultures, in which the bioreactor permits harvesting of the cells produced therein without disrupting the culture.

According to one feature of the invention, the above and other objects are carried out according to the present invention by a bioreactor for the ex vivo maintenance and growth of mammalian cells, comprising a substantially circular cell growth chamber defined between a substantially planar cell bed and a gas permeable, liquid impervious membrane, a media inlet communicating with a radially central portion of the cell growth chamber, and a plurality of media outlets radially outwardly spaced from the media inlet by a distance sufficient for cell growth to occur between the inlet and the outlets. The outlets are substantially equiangularly circumferentially spaced about the cell growth chamber.

According to another feature of the invention, the bioreactor for the ex vivo maintenance and growth of mammalian cells comprises a bioreactor top and a bioreactor base fluidtightly integrated so as to form an interior volume, a gas permeable, liquid impervious membrane fluidtightly separating the interior volume into upper and lower portions, a substantially planar cell bed member positioned in the lower portion and extending substantially parallel to said membrane, the membrane and the cell bed member defining a substantially circular cell growth chamber therebetween, a gas chamber in the upper portion and in fluid communication with the membrane for supplying oxygen to the cell growth chamber, a media inlet in the cell bed member and communicating with a radially central portion of said cell growth chamber, and a plurality of media outlets in the cell bed member and radially outwardly spaced from said media inlet by a distance sufficient for cell growth to occur in a cell growth bed between the inlet and the outlets. The outlets are substantially equiangularly circumferentially spaced about the cell growth chamber.

According to yet another feature of the invention, a cell cassette for the ex vivo maintenance and growth of mammalian cells comprises a bioreactor having a substantially circular cell growth chamber defined between a substantially planar cell bed and a gas permeable, liquid impervious membrane, a media inlet communicating with a radially central portion of the cell growth chamber, and at least one media outlet radially outwardly spaced from the media inlet by a distance sufficient for cell growth to occur in a cell growth bed between the inlet and the at least one outlet, and a drip chamber receiving media from the at least one outlet for controlling a flow rate of the fluid through said cell growth chamber at a constant value.

According to yet another feature of the invention, a disposable, self contained cell cassette for the ex vivo maintenance and growth of mammalian cells comprises a casing, a bioreactor in the casing, and a non-volatile memory for recording process data for the cassette.

According to yet another feature of the invention, a system for the ex vivo maintenance and growth of mammalian cells comprises a disposable, self contained cell cassette including a casing, a bioreactor in the casing, a non-volatile memory for recording process data for the cassette, a memory interface, and at least one fluid port on the casing and connected to said bioreactor, a system manager separate from the cassette and including a computer having an interface with said memory interface for transferring process data between the computer and the memory, and an incubator unit matable with the at least one fluid port and having a computer connected to the computer of the system manager and matable with said the memory interface.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

DETAILED DESCRIPTION OF THE PREFERRED EMBODIMENTS

Preferred embodiments of the present invention will now be described with reference to the attached figures, in which the same reference numerals are used to denote the same or corresponding part throughout the several views.

The stem cell production system according to the present invention represents technology for the ex vivo growth and expansion of human stem and hematopoietic progenitor cells, as well as other mammalian, including human, cells. The system is intended to provide cells in sufficient volume and with the necessary characteristics to provide for therapy or treatment such as a complete bone marrow transplantation or a nadir prevention/rescue resulting from therapies such as high dose chemotherapy or radiation. These cells are grown from a small starting population of cells normally obtained from the bone marrow. The use of the human stem cell production system provides for production of cells that can be infused to augment recovery of a compromised hematopoietic system.

Figure 1:
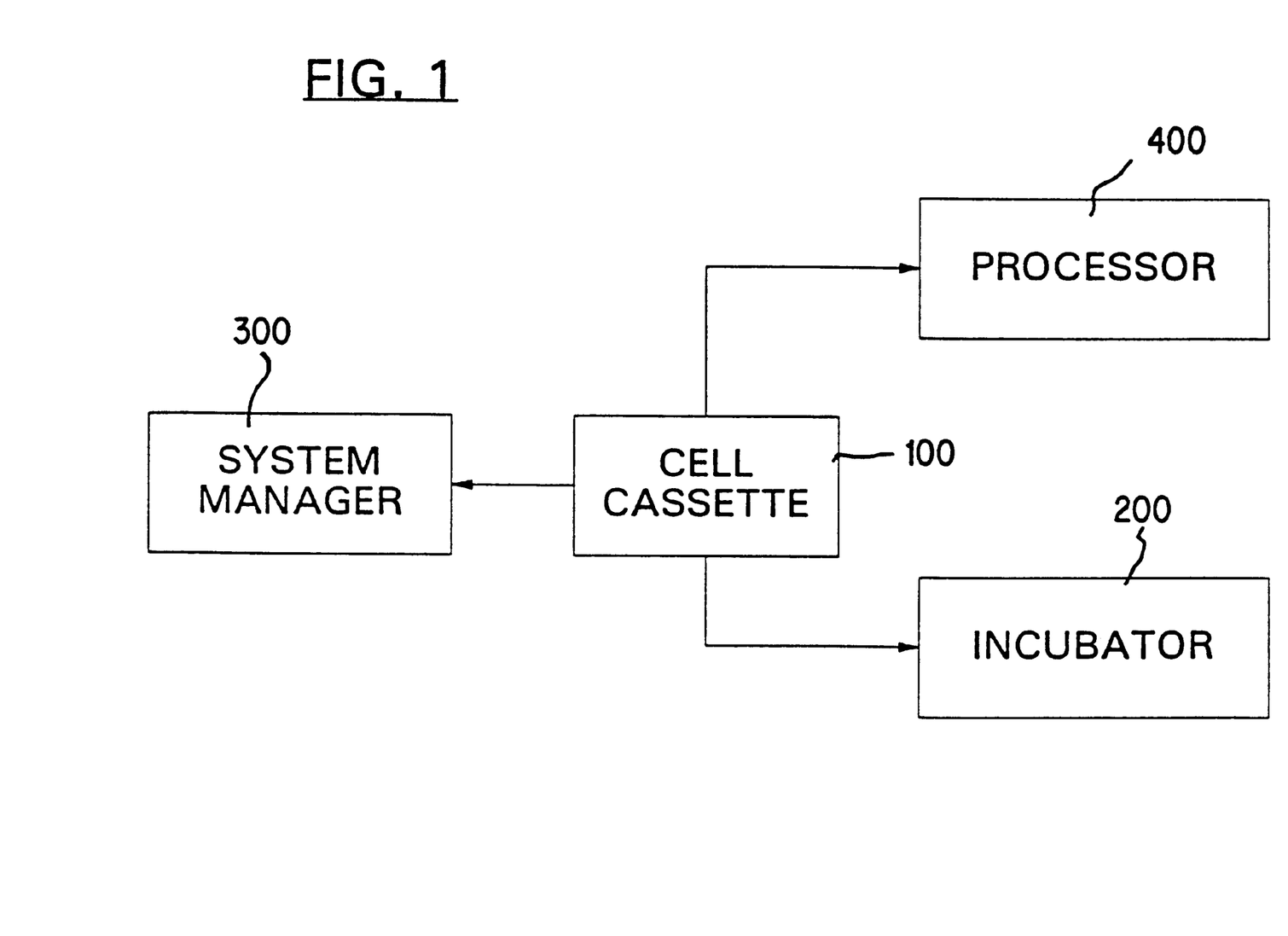
FIG. 1 is a diagram illustrating the major components of the cell production system according to the invention.
Figure 2:
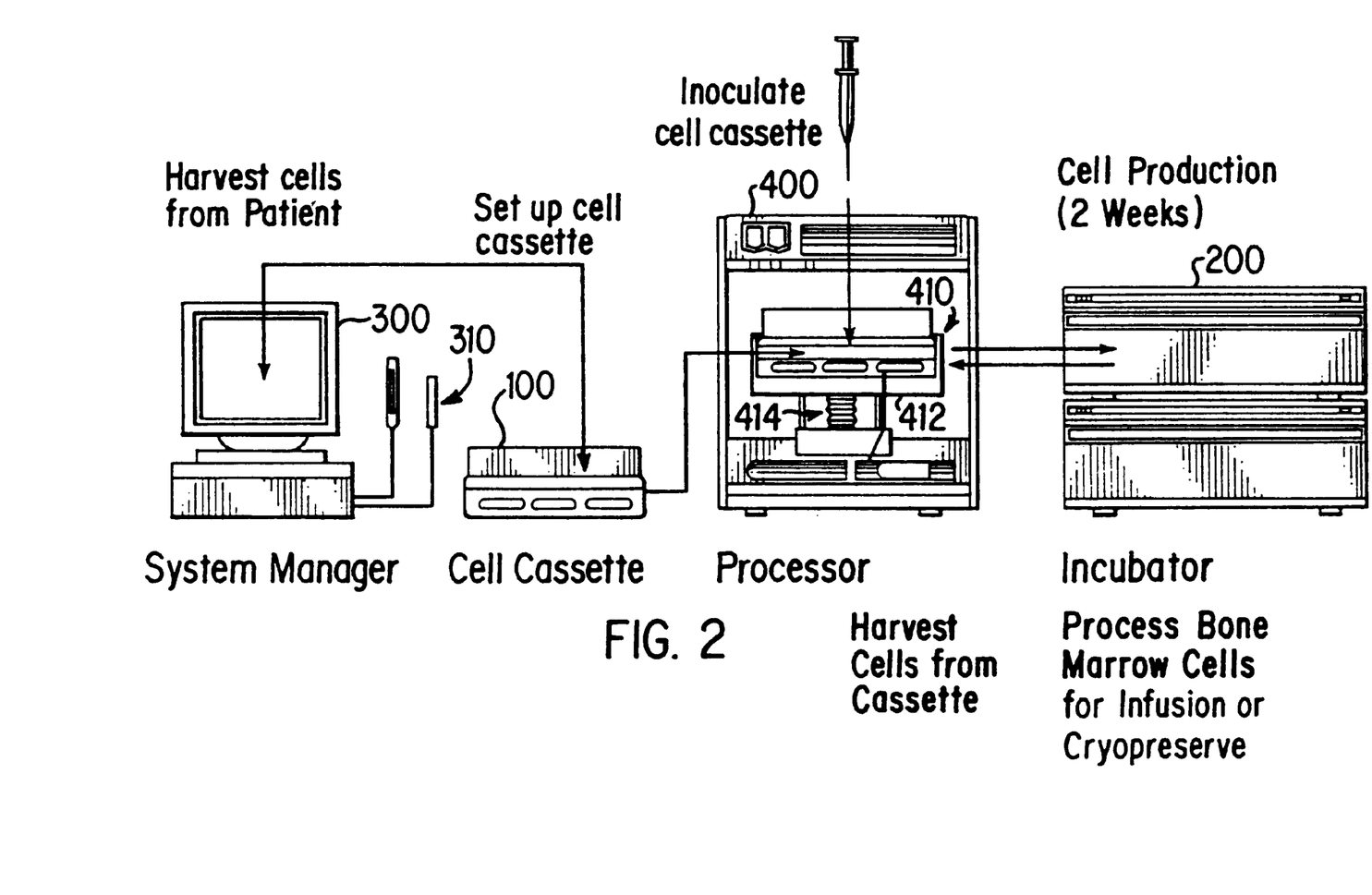
FIG. 2 is a schematic illustration of one embodiment of the overall system of FIG. 1.
Figure 3:
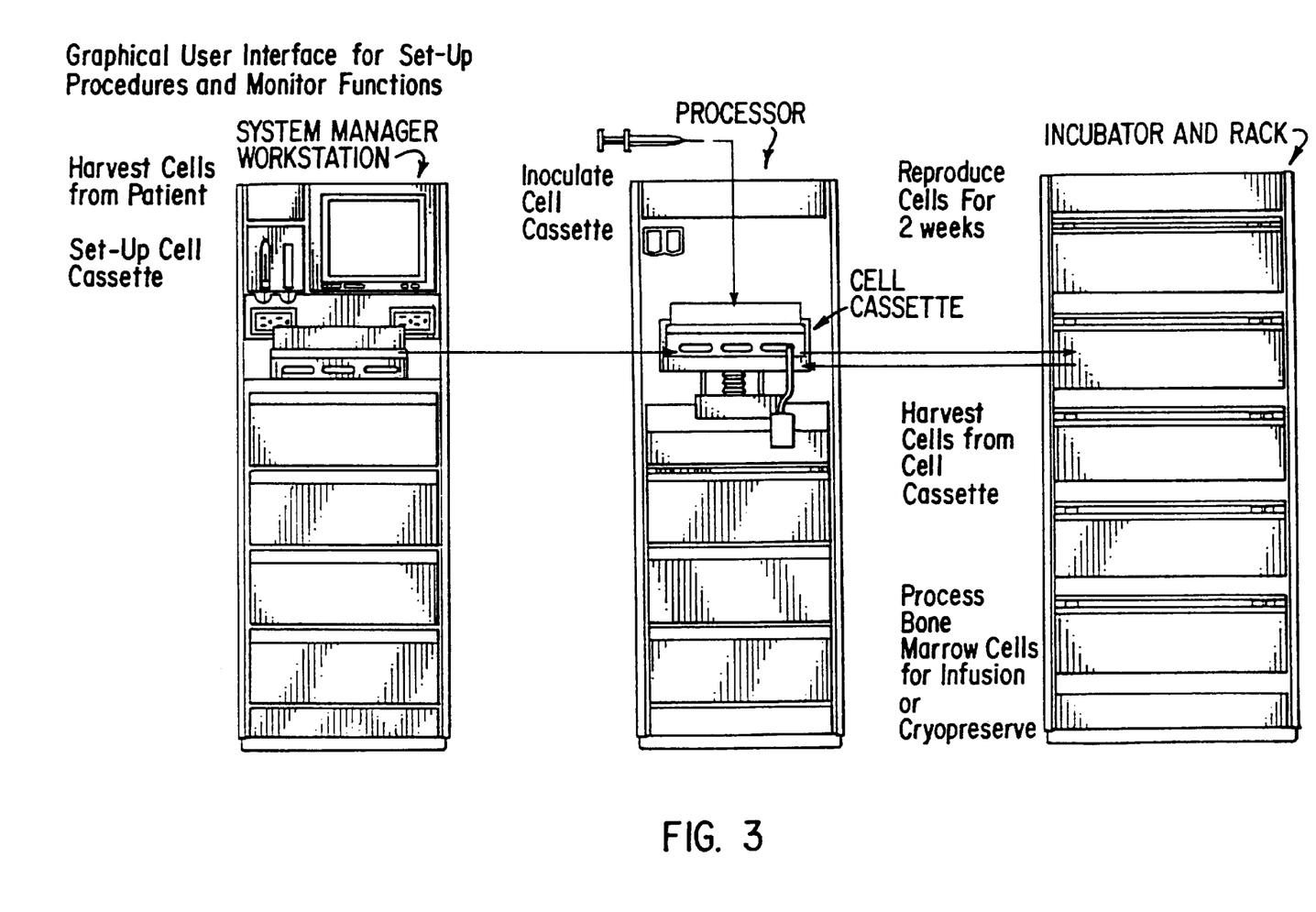
FIG. 3 is a schematic diagram illustrating another embodiment of the overall system of FIG. 1.
Figure 4A:
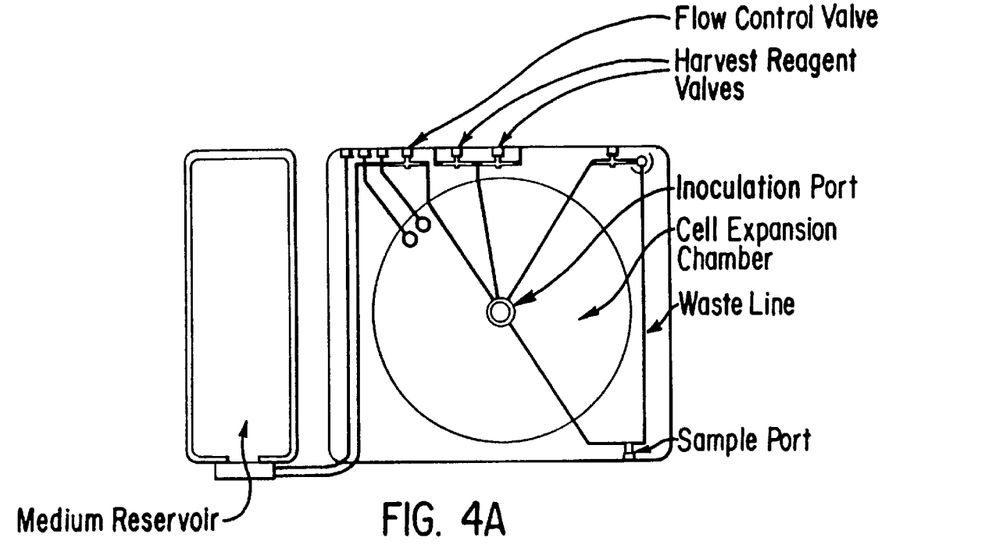
FIGS. 4A and 4B are schematic top and side views of an embodiment of a cell cassette according to the invention.
Figure 4B:
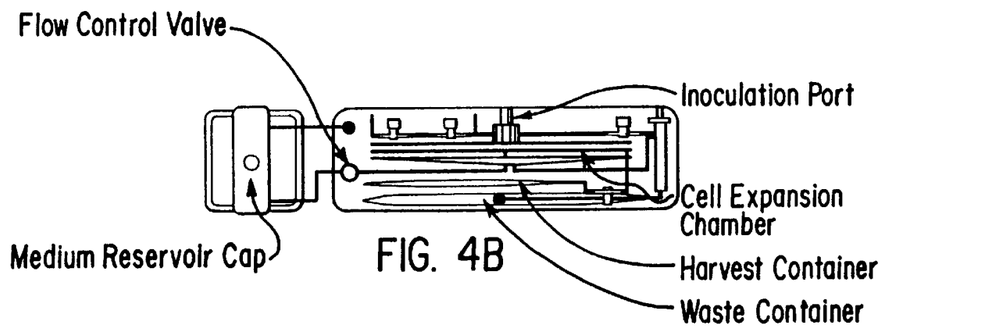

Referring to FIG. 1, the major components of the stem cell production system include a disposable cell cassette 100 where the growth and expansion of cells takes places, a hardware incubator unit 200 and companion hardware, a system manager 300 that controls the biological and physical environment during the expansion process, and a processor unit 400 that facilitates the initial filling and inoculation of cells, as well as the final harvest of cells at the completion of the expansion process.

As described in the aforementioned copending application Ser. No. 08/178,433, simulating bone marrow for the purpose of ex vivo growth and expansion of mammalian stem and hematopoietic progenitor cells requires, amongst other things, a uniform oxygen concentration and a uniform supply of a nutrient carrying perfusing liquid for all of the cells being cultured. A primary function of the cell cassette 100 is to provide the cell growth bed and to contain the oxygen and perfusing liquid flow components in a functionally closed environment in which the cell production can occur.

Figure 5:
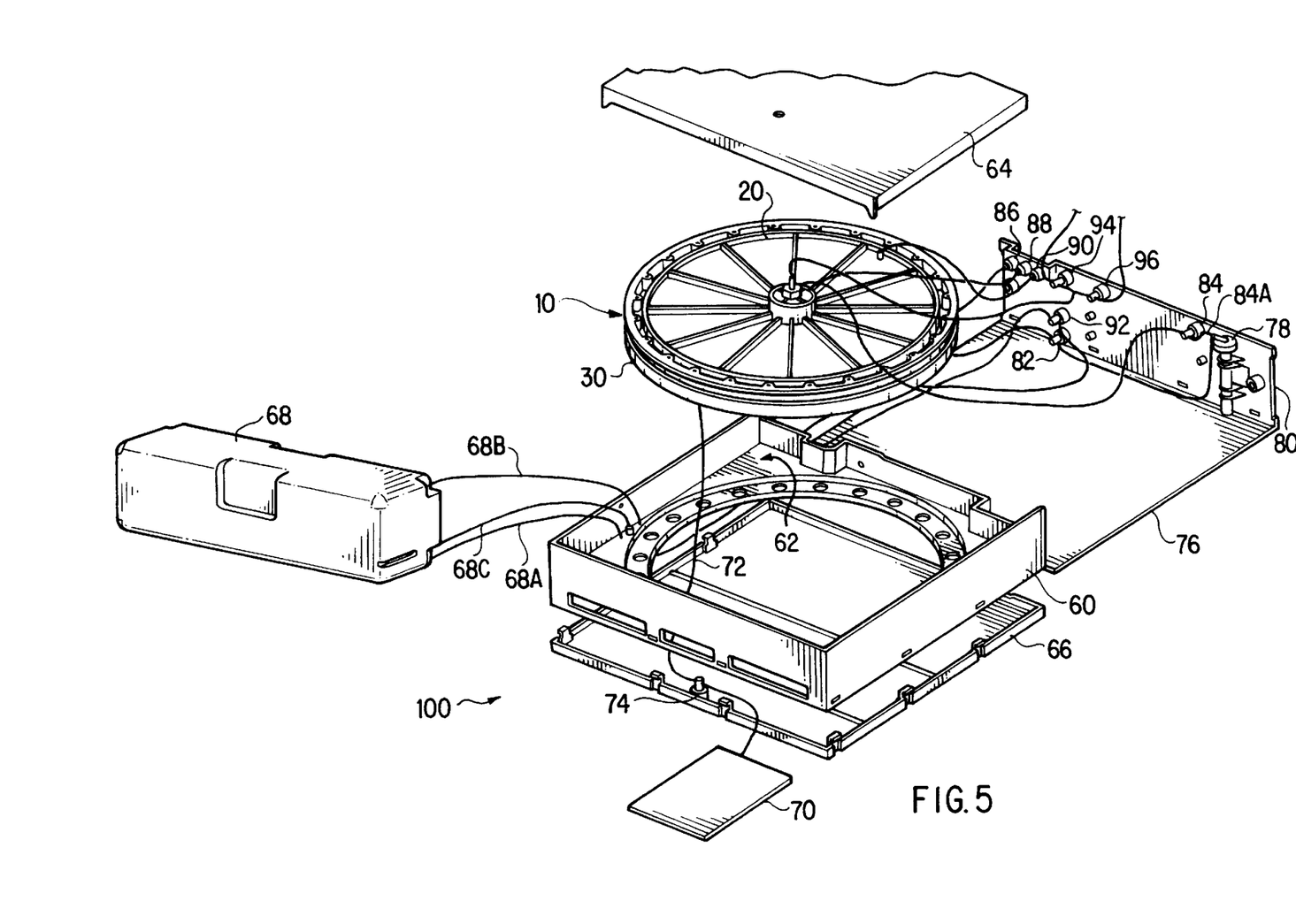
FIG. 5 is an exploded view of the cell cassette of FIGS. 4A and 4B.

Referring to FIG. 5, the primary element of the cell cassette is a disc-like bioreactor 10 having a preferably circular outer periphery. The bioreactor is formed of four main components: a top 20, a base 30, a cell bed disc 40 and a gas permeable, liquid impervious membrane 50.

Figure 7:
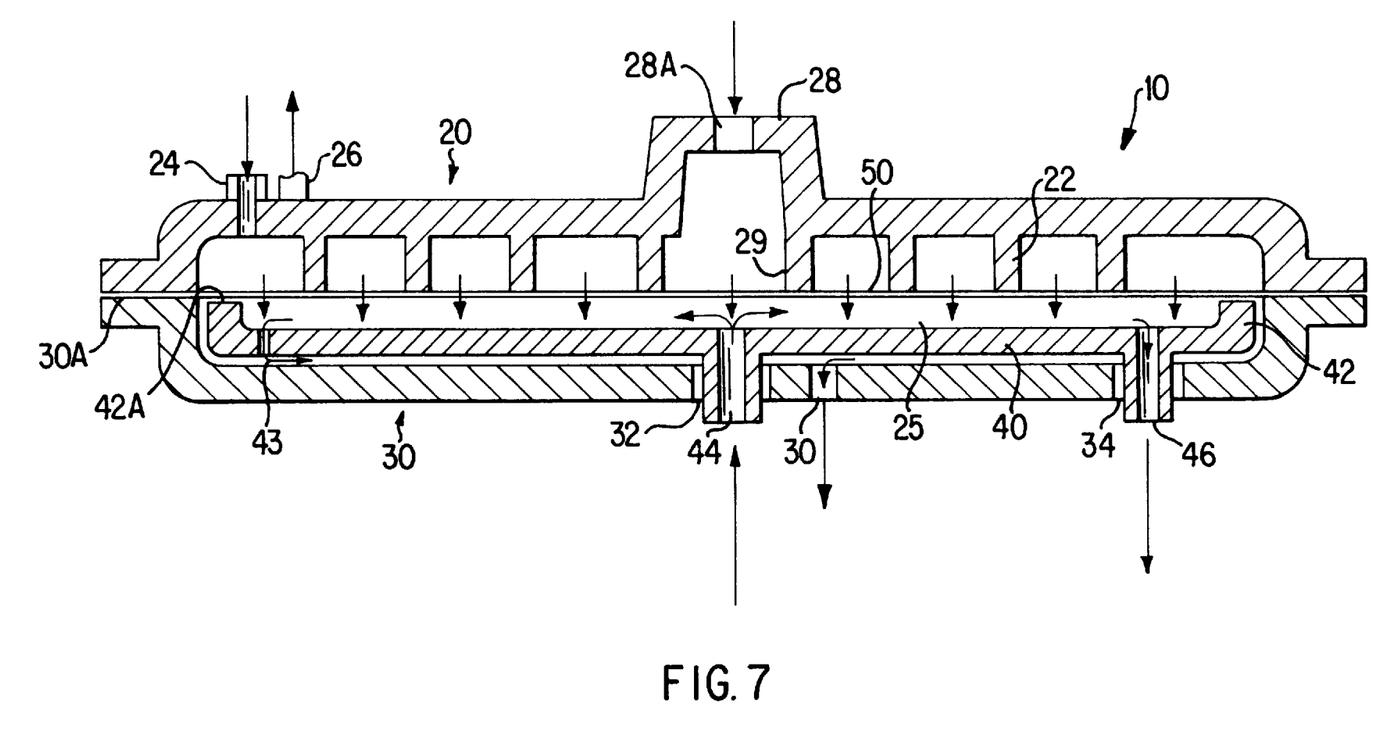
FIG. 7 is a schematic sectional view of the bioreactor portion of a cell cassette according to the present invention.

As shown schematically in FIG. 7, the top 20 of the bioreactor is fluid-tightly secured to the base 30, for example by screws or bolts, at its radially outer periphery. The membrane 50 is clamped between the top and the base and is tightly stretched so as to separate the interior volume of the bioreactor into upper and lower portions.

The cell bed disc 40 is located within the lower portion of the interior of the bioreactor. It has generally disc shape with an upwardly extending annular lip 42 at its outer radial periphery. Following their inoculation, cell growth occurs in a cell growth bed 25 defined between the upper surface of the disc 40, the lower surface of the membrane 50 and the annular lip 42. The upper surface A of the annular lip 42 is coplanar with the upper surface of the flange 30A of the base 30 when the disc 40 is fitted in the base, so that membrane 50 can cooperate with the lip 42 to seal the cell growth bed 25.

The disc 40 of the cell bed has a radially central growth media supply port 44, which extends downwardly through the base 30 to the exterior of the bioreactor. It also has a harvest port 46 near the radially outer limit of the cell bed, i.e., just inside the lip 42. The port 46 also extends through the base to the exterior of the bioreactor. Finally, the base has a plurality of, e.g., 24, waste media discharge apertures 48 extending entirely through its thickness from top to bottom. The apertures 48 are equiangularly spaced about the radially outer periphery of the disc 40, immediately adjacent the lip 42.

A nutrient rich growth media is supplied to the media supply port 44. The growth media may be a standard growth medium such as that described in U.S. patent application Ser. No. 08/143,751, filed Nov. 1, 1993, now abandoned, and may have a serum supplement such as fetal bovine serum, horse serum or human serum. It may also be serum free. Growth factors and reagents such as glutamine may also be added as necessary. The growth media may be supplied in premixed bags or may be modified on site.

From the media supply port, the growth media enters the cell bed 25 and flows radially outwardly toward the radial periphery of the disc 40. As it does so, it supplies nutrients to, and removes waste products from, the cells being cultured therein. It is discharged as waste media from the cell bed by flow through the plurality of apertures 48, as shown by arrows in FIG. 7.

Because of the radially outward flow of the perfusing liquid and the arrangement of the outlet apertures 48, the cells within the cell culture bed are uniformly perfused with nutrients. For example, the radial flow of the perfusing liquid to a plurality of equiangularly spaced outlet apertures promotes a uniform fluid flow from the inlet, and over the cell bed to the perimeter outlet locations on the circumference of the cell bed.

The base 30 has apertures 32 and 34 through which the ports 44 and 46 can extend in a fluid tight manner, for example, via seals (not shown) between the apertures and the ports. It also includes a generally centrally located outlet port 36 for the waste media. The waste media from the apertures 48 flows radially inward, through the space between the bottom surface of the disc 40 and the top surface of the base 30, to the port 36 and is thereby discharged from the bioreactor. The port 36 may be co-axial, but can also be slightly offset from the radial center of the base 30 in order to accommodate the aperture 32 for the media inlet port 44.

The bioreactor top 20 is secured to the base 30 in a fluid tight fashion, with the membrane 50 therebetween, as mentioned above. A concentric labyrinth path of ribs extend inwardly from the top 20 to support the membrane 50 against distortion due to the fluid pressure of the perfusion liquid in the cell bed. The ribs 22 maintain a precise spacing between the top surface of the disc 40 and the bottom surface of the membrane 50, i.e., a precise thickness for the cell growth bed. This thickness is preferably no more than 4 mm in order to assure adequate oxygenization of the cells within the cell growth bed.

The ribs 22 also form a labyrinth-like gas chamber through which an oxygenization fluid, such as air, can flow to supply oxygen which is diffused through the membrane and into the cell bed. The two ends of the labyrinth may be adjacent one another so that the oxygenizing air can be supplied to the gas inlet port 24 and discharged through the gas outlet port 26.

A bell-like raised center port 28 is formed at a radial center of the top 20 and forms a chamber sealed by the annular rib 29 bearing against the membrane. Cells can be inoculated into the cell growth chamber via a center port septum 28A. For this, a non-latex needle septum is secured to a port feature with an air-tight band for access directly to the cell residence area.

Figure 8A:
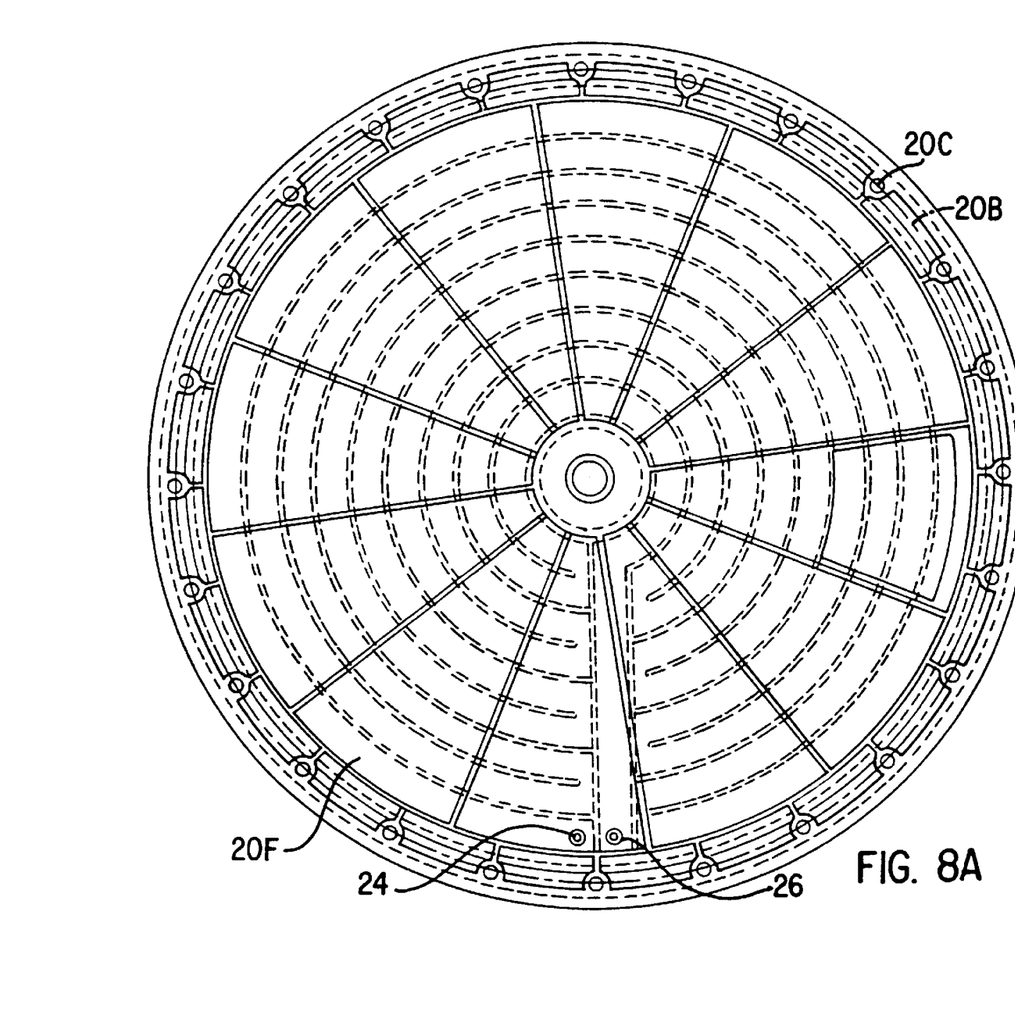
FIGS. 8A and 8B are top and sectional views of a bioreactor cover according to an embodiment of the invention.
Figure 8B:
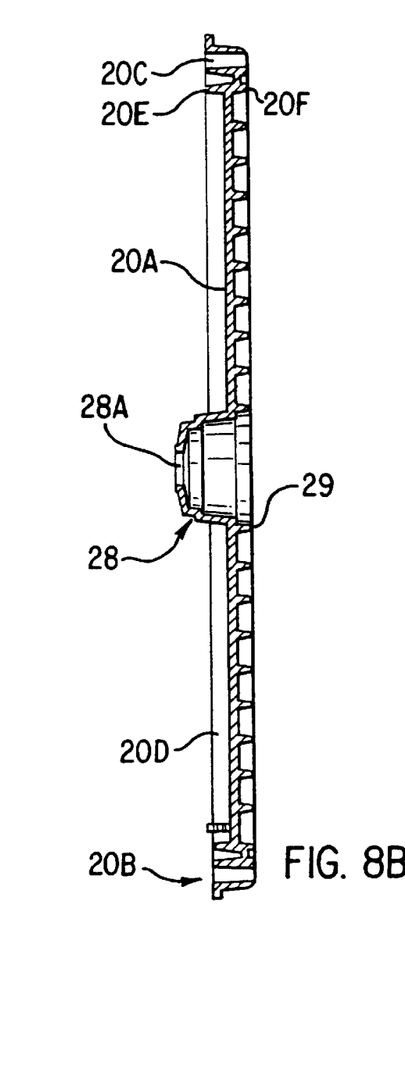
Figure 9A:
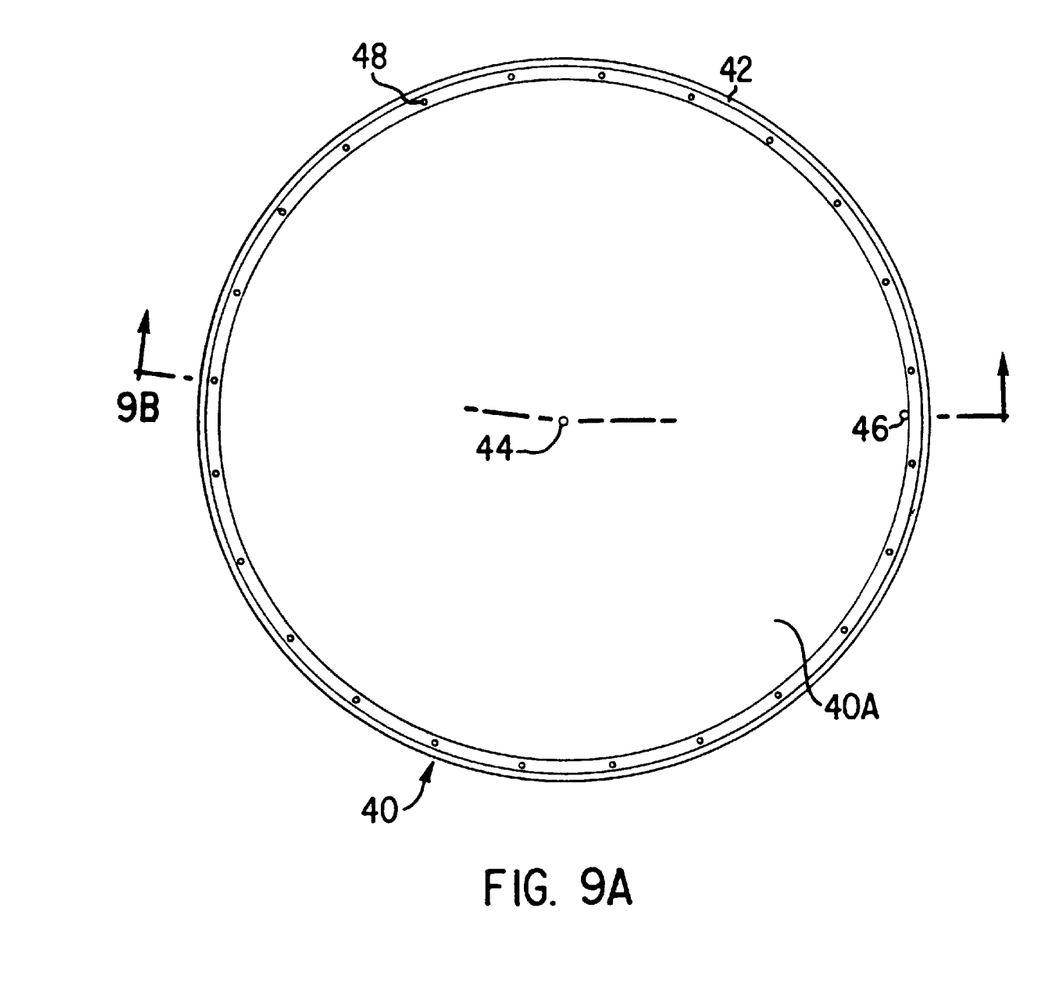
FIGS. 9A and 9B are top and sectional views of a bioreactor cell bed disc according to an embodiment of the invention.
Figure 9B:
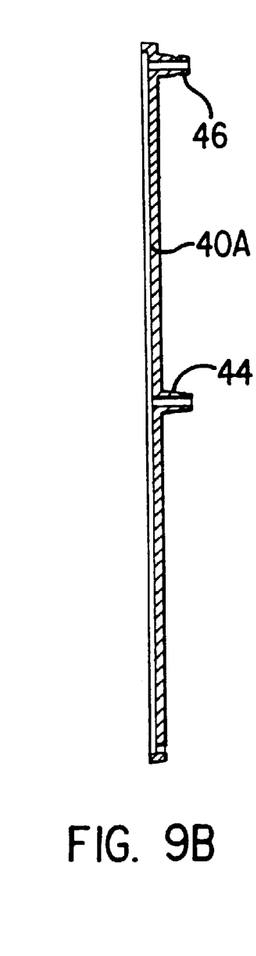
Figure 10A:
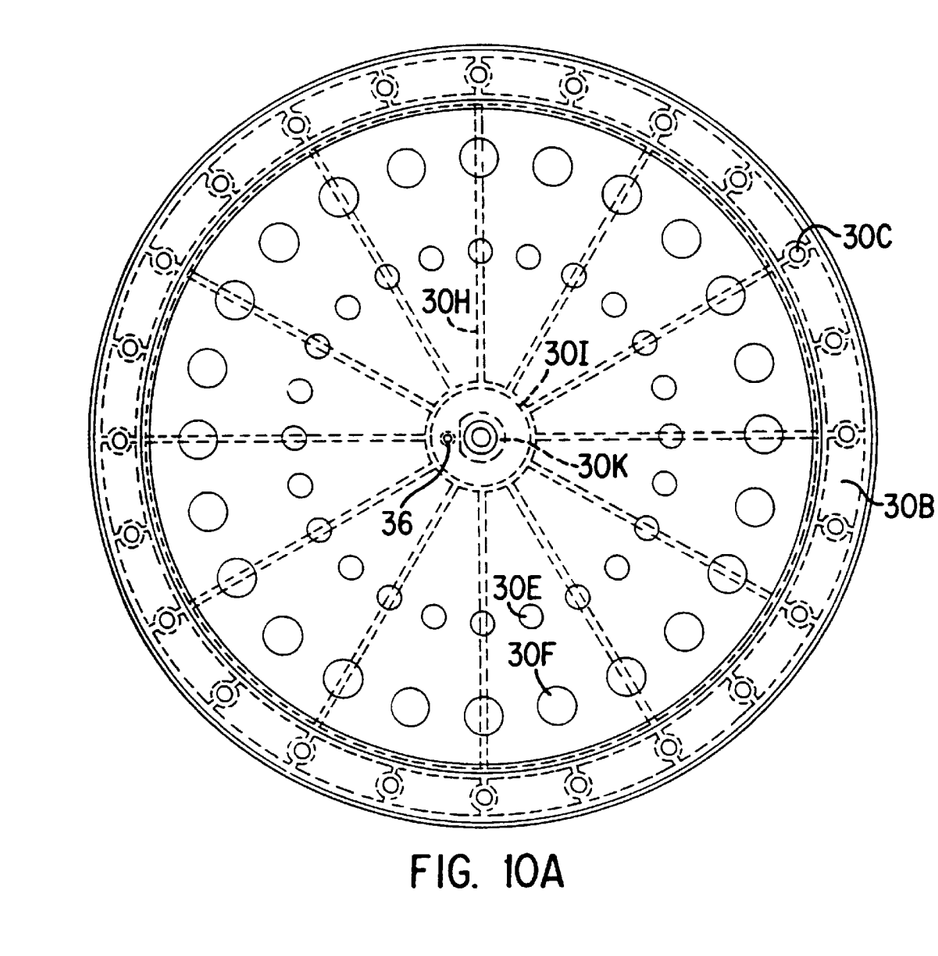
FIGS. 10A and 10B are top and sectional views of a bioreactor base according to the present invention.
Figure 10B:
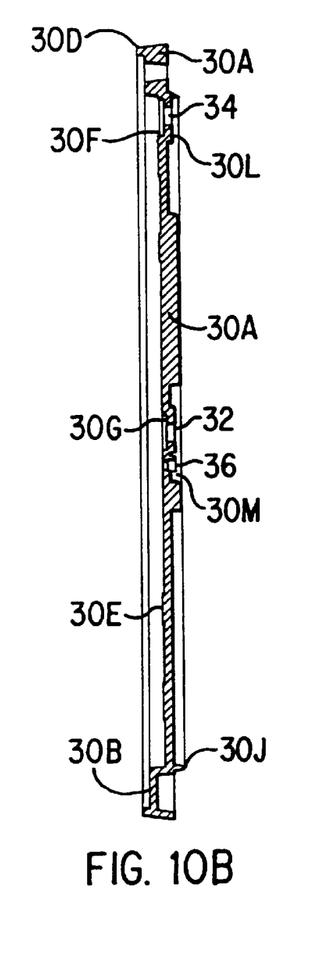

Referring to the detailed illustrations of the bioreactor top, base and cell bed disc shown in FIGS. 8 through 10, the bioreactor top 20 is shown in FIGS. 8A and 8B. The top 20 is preferably formed of an injection molded transparent, non-reactive plastic such as polystyrene or PETG. It has a generally disc-like main portion 20A bounded at its radially outer periphery by a flange 20B. The flange 20B has an equiangularly spaced plurality of bolt holes 20C, through which may pass bolts (not shown) for securing the top 20 to the base 30.

The raised center port 28 has a generally bell shape and a central septum 28A. The septum is a gas and liquid impermeable barrier that may be pierced by an injection needle and is self-sealing when withdrawn. An equiangularly spaced plurality of radial reinforcing ribs 20D extend from the main portion 20A between the center port 28 and an annular reinforcing rib 20E adjacent the rim 20B.

The ribs 22 are generally annular in orientation and form a labyrinth 20F as shown by dash lines in FIG. 8A. The labyrinth is convoluted such that an oxygenizing gas is able to flow through a gas chamber defined thereby over the entire cell growth bed. The opposite ends of the labyrinth are preferably adjacent one another at the radially outer end of the main portion 20A. An inlet port 24 and the outlet port 26 communicate with the opposite ends of the labyrinth.

A radially innermost rib 29 is a continuous annulus which, in cooperation with the membrane 50, seals the gas chamber defined by the labyrinth from the interior of the central port 28. A radially outermost continuous rib 20F defines the outermost limit of the labyrinth. The tips of all of the ribs 20F, 22 and 29 are coplanar with the bottom surface of the flange 20B so that the ribs seal with respect to the membrane 50 when the bioreactor is assembled.

Referring to FIGS. 9A and 9B, the cell bed disc 40 is preferably also formed of an injection molded transparent, non-reactive plastic such as polystyrene or PETG. It has a generally disc-like main portion 40A bounded at its radially outer periphery by the annular lip 42. The upper surface of the main portion is generally smooth and unobstructed and forms a surface of adhesion for the cell colony being cultured.

Referring to FIGS. 10A and 10B, the base 50 is preferably also formed of an injection molded transparent, non-reactive plastic such as polystyrene or PETG. It also has a disk-like main portion 30A bounded by a raised peripheral flange 30A having an upper surface 30B and bolt holes 30C. When assembled, the disc 40 fits entirely within the bounds of the peripheral flange 30A with the surface A closely adjacent, and coplanar with, the surface 30B. Moreover, the bolt holes 30C align with the bolt holes 20C when the top 20 is assembled with the base 30, so that bolts can pass therethrough for securing the top and base. A peripheral lip 30D extends upward from the radially outer edge of the flange 30B to position and retain the membrane 50 during assembly of the bioreactor.

The upper surface of the main portion 30A has a plurality of raised regions 30E which support the bottom surface of the disc 40 and maintain a separation between disc 40 and base 30, thereby defining the fluid path for the return flow of the waste media to the central outlet port 34. Recesses 30F and 30G surround each of the apertures 32 and 34, and can house resilient elements for sealing the apertures.

A plurality of radial supporting ribs 30H extend from the bottom surface of the base and extend between the annular supporting ribs 30I and 30J. Annular reinforcing enlargements 30K, 30L and 30M surround the apertures 32, 34 and 36, respectively.

In assembling the bioreactor, Appropriate seals are positioned at the apertures 32 and 34, and the disc 40 is positioned within the base 30 with the nipples of the ports 44 and 46 sealingly extending through the respective apertures as shown schematically in FIG. 7. The membrane 50 is then placed over the disc 40 and the flange 30A, and is held within the lip 30D. The top 20 is then placed over the base with the bolt holes 20C and 30C in alignment, and bolts are passed through the bolt holes and tightened to unify the bioreactor. At this time, the outer annular rib 20F will clamp the membrane 50 against the radially innermost portion of the surface 30B to seal the interior of the bioreactor.

Figure 6:
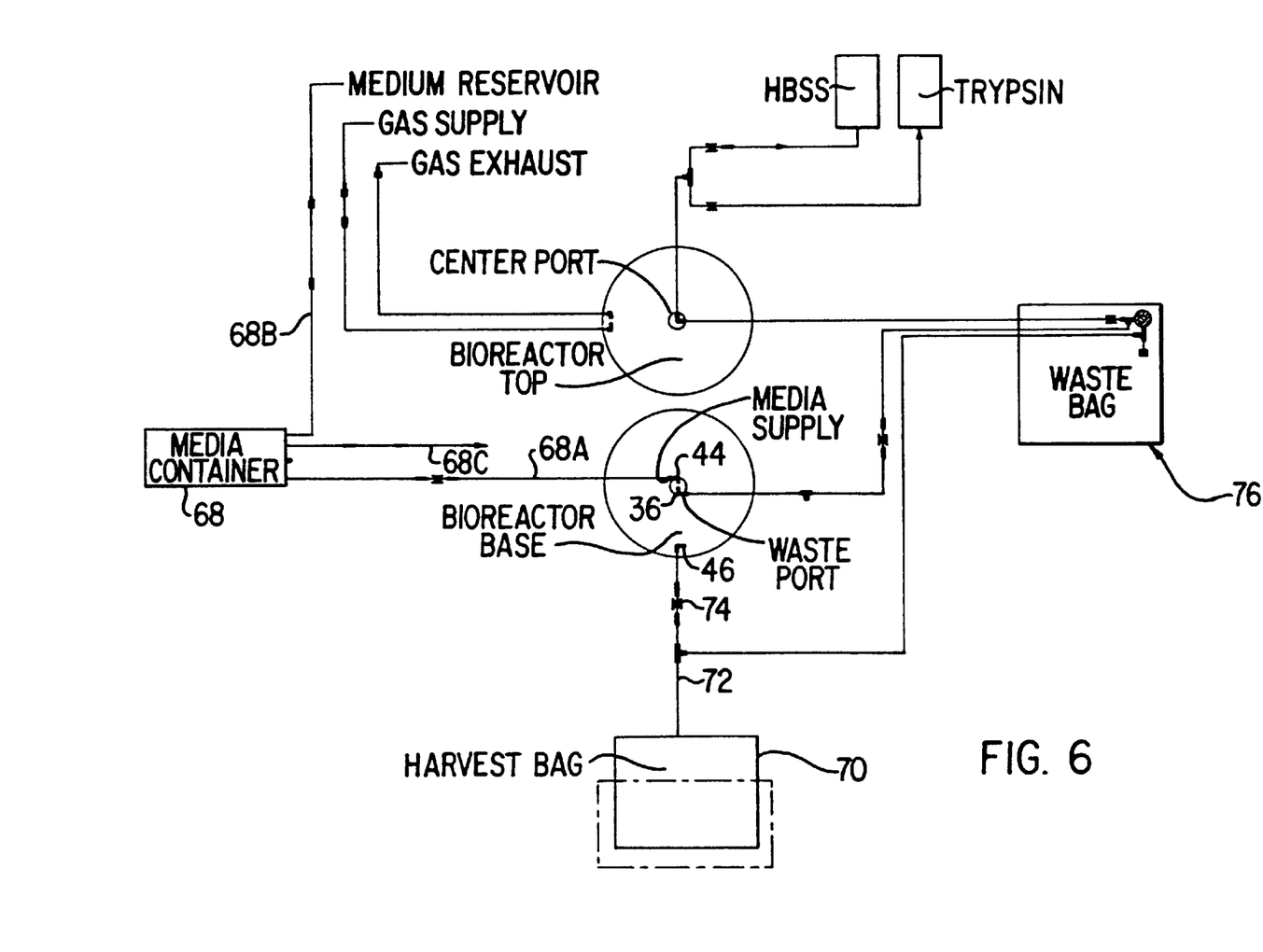
FIG. 6 is a schematic view showing fluid conduit routing in the cell cassette according to an embodiment of the invention.

Referring to the schematic FIGS. 5 and 6, the bioreactor 10 is held within a casing of a cell cassette 100 and forms a preassembled, disposable unit. The bioreactor is secured to a cassette base 60 of the cassette casing. In the illustrated embodiment, the base 60 has a support flange 62 with a central aperture having a plurality of holes. The bolts used to secure the top to the base of the bioreactor 10 can also extend through these holes for securement of the bioreactor to the cassette base 60. The cassette base is closed from above by a top 64 and from below by a tray 66, and a media supply container 68 is mounted to a front surface of the cassette base 60 for supplying a growth media to the bioreactor. The media supply container 68 is provided with a media supply line 68A connected to the media inlet port 44 of the bioreactor. Pressurized air from an air pump is supplied to the air space above the media in the media supply container via the line 68B, and in this way the growth media is pressurized so as to provide a constant flow rate of media to the cell growth bed 25 in the bioreactor. Additional growth media is supplied to the container via the media container strain relief conduit 68C.

A cell harvest bag 70 is connected to the harvest port 46 of the bioreactor via the conduit 72 and the harvest valve 74.

A waste media bag 76 is positioned below the bioreactor and rests on the tray 66 of the cell cassette. It receives waste media from the bioreactor via a drip chamber device 78 attached to a valve plate 80 at the rear of the cell cassette. The drip chamber includes a siphon break to permit a precisely controlled rate of flow, thereby assuring a constant flow rate of fluid through the cell bed of the bioreactor. A drip counter (not shown) can be associated with the drip chamber device. It counts the drops of waste media to detect the media flow rate.

The waste media reaches the drip chamber device via a waste valve 82. Gas pressure at the center port 28 of the bioreactor is used to regulate flow through the drip chamber, via the center port valve 84 and the line 84A.

Also attached to the valve plate are an air pump supply port 86 for supplying compressed air at a constant pressure to the media supply container via the air pump supply line 68B; gas in and out ports 88 and 90 for supplying fresh oxygenizing gas to, and discharging spent oxygenizing gas from, the bioreactor; a media supply valve 92 connected to the media container strain relief line 68C; HBSS valve 94; and trypsin valve 96.

Each cassette also includes a "key" containing a non-volatile memory device and a clock. Before use, the key of the cassette is initialized with tracking data, protocol commands and real time via the system manager 300. The key is used by the system electronics during the cell production process to record pertinent data as well as to access the protocol commands.

In use, a sterile, single use disposable cell cassette 100 is supplied in a protective package. It includes the medium supply reservoir 68, a supply pump (not shown), the bioreactor 10, the waste reservoir 76, the harvest reservoir 70, a key and the necessary plumbing, valving and packaging to interconnect and support the components.

Figure 11:
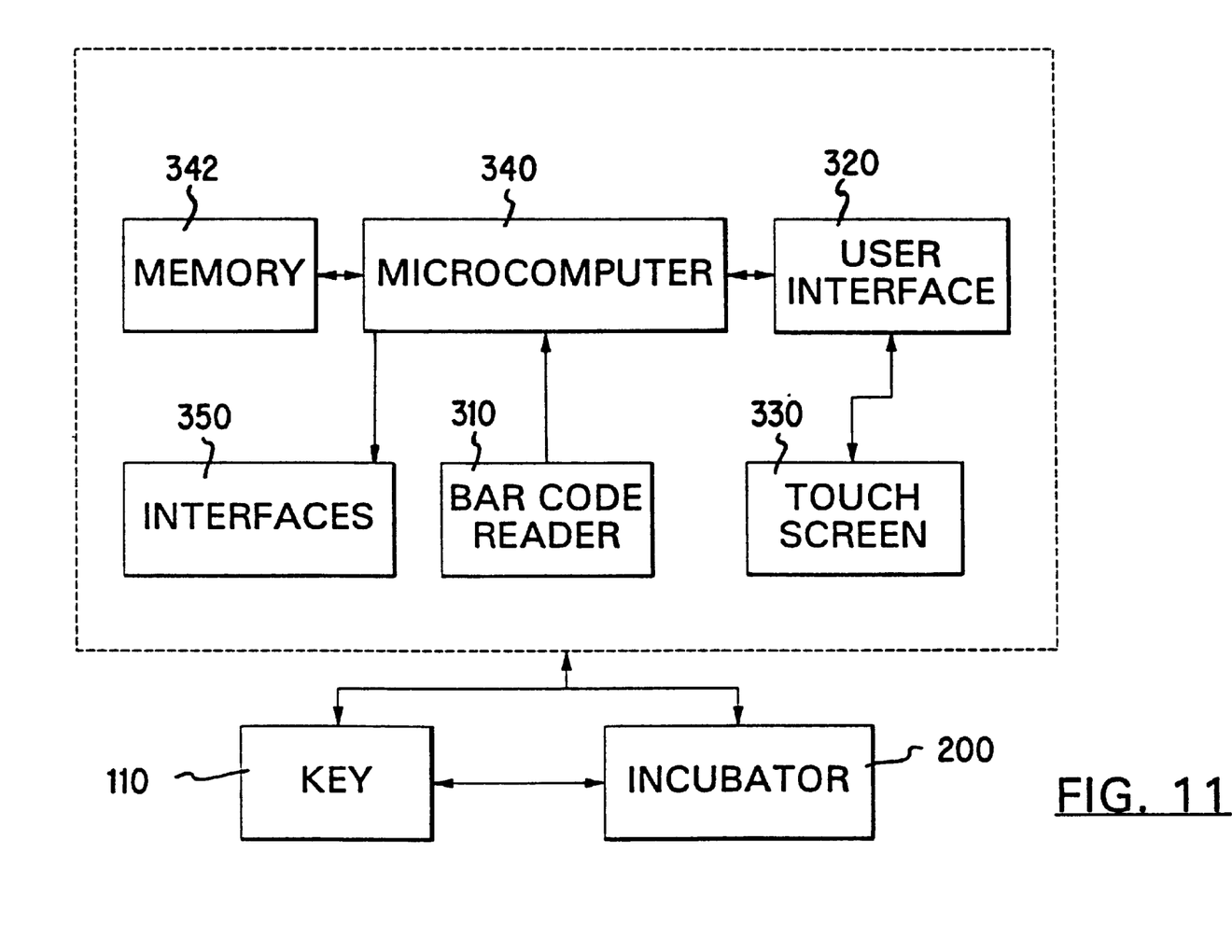
FIG. 11 schematically illustrates the control system of the system manager.

In operation, the key is first initialized by the system manager 300. For this purpose, a bar code reader 310 of the system manager reads a bar code associated with the cassette and the key is supplied with initial data via an interface. The system manager is designed around an interactive graphic user interface 320 and color touch screen 330. The system manager includes a microcomputer 340 having a memory 342 for program and data storage, the bar code reader 310, interfaces 350 for the key and up to 50 incubators, a printer and an optional keyboard (not shown).

Primary functions of the system manager 300 include set up for inoculation and harvest; initializing the key with tracking information; circuit protocol and real time; monitoring all normal and abnormal activity at each incubator; and printing reports and labels.

Once the key has been initialized by the system manager, it is transferred to the processor 400. The processor can operate independent of the system manager, or can be connected to the system manager. The processor includes a multiaxis gyrator ("wobbulator") 410. The wobbulator includes a support table 412 onto which the cassette can be secured. The wobbulator has mechanical linkages 414 for pivoting the support table 412 about two orthogonal horizontal axes.

When a cell cassette is loaded in the processor 400 and clamped onto the support table 410, and the key indicates that inoculation is required, the processor provides an automatic sequence of inoculation operations. For example, the inoculation sequence can consist of the following steps. First, the wobbulator table 412 is brought to a horizontal home position. The cell cassette 100 is then primed with growth media to the required volume, employing gravity feed of media from the reservoir 68. During this time, the harvest valve 74 is closed and the waste valve 82 is open so that media in the cell growth chamber 25 can flow through the apertures 48 but not through the harvest port 46. The cell cassette is then tilted to generate a bubble to be used in distributing the cells. The cell growth chamber is then inoculated with cells. This may be done via a hypodermic syringe passing through the center port septum and the membrane. The wobbulator then oscillates the cell cassette according to a predetermined program to distribute the cells on the upper surface of the disc 40. At this time, the bubble aids in the even distribution of the cells within the cell growth chamber. Remaining air is then purged through the center port and the cassette is removed from the processor. The cassette is then ready for incubation.

The cassette is then placed in the incubator 200. The incubator is an instrument capable of accepting cell cassettes for cell production. It can take the form of a rack 210 to which plural cassettes are attached. It mates with the cassette to provide power and connections for the supply of additional media. It is also connected to the system manager 300 and to the key 110 for storing the incubation start time and date on the key, and incubation data is continually provided to the key during the incubation sequence. The key 110 also receives information on abnormal events, such as alarms or power failures, the amount of medium used and the incubator identification. The incubator controls the flow of medium through the growth chamber, the temperature of the growth medium reservoir 68, and the concentration, pressure, e.g., 40–60 psi and flow rate of gases delivered to the gas chamber in the bioreactor, based on control settings stored in the key and initialized by the processor. The incubator also monitors various safety/alarm parameters to assure that the cell production process is proceeding as expected. This can be done for a number of incubators through the system manager computer or by use of an independent incubator computer.

Finally, at the completion of incubation, cells may be harvested from the cell cassette in the following manner. The cassette is returned to the processor and placed on the wobbulator platform 412 in a level or home condition. He waste valve 82 is closed and the harvest valve 74 is opened. Harvest reagents such as trypsin and HBSS (Hanks Balanced Salt Solution) are introduced into the growth chamber 25 via the center port septum, e.g., from a prepared package, causing the cells to separate from the surface of the cell bed disc 40. The cell cassette is then tilted by the wobbulator so that the harvest port 46 is at the lowermost position of the cell, and the contents of the growth chamber are drained by gravity into the harvest bag 70. Additional trypsin is added and the cell cassette is tilted with a variable motion so as to slosh the trypsin within the cell bed. The washed liquid is then gravity drained into the harvest bag. This step is then repeated with HBSS.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A computer program product in a bioreactor system for ex vivo maintenance, and growth of mammalian cells, comprising:

a transportable cassette having a gas chamber and cell growth chamber, environmental conditions in said cell growth chamber being dominated by a media flowing therethrough and environmental conditions in said gas chamber being dominated by a gas flowing therethrough, said transportable cassette having a computer storage medium encoded with a computer code mechanism that when executed by a processor in the bioreactor system and external to the transportable cassette controls environmental conditions in a bioreactor portion of the system to be suitable for the ex vivo maintenance and growth of the mammalian cells, said computer program code mechanism including, a media flow code mechanism having a media flow rate parameter embedded therein and being accessible to said processor when maintaining a predetermined media flow rate through the cell growth chamber so as to maintain the environmental conditions to be suitable for the maintenance and growth of the mammalian cells.

2. The computer program product of claim 1, wherein said computer program code mechanism further comprises:

a temperature control mechanism having a temperature paramctcr embedded therein and being accessible to said processor when maintaining a predetermined temperature of said bioreactor portion.

3. The computer program product of claim 1, wherein said computer program code mechanism further comprises:

a gas mixture and gas flowrate code mechanism having at least one of a gas mixture parameter and a gas flowrate parameter embedded therein and being accessible to said processor when maintaining a predetermined gas conditions in said gas chamber.

4. The computer program product of claim 1, wherein said computer program code mechanism further comprises:

a gas concentration code mechanism having at least one of a gas concentration parameter embedded therein and accessible to the processor when maintaining a predetermined gas concentration in said gas chamber.

5. The computer program product of claim 1, wherein said media flow rate parameter, being a time-varying parameter.

6. The computer program product of claim 1, wherein said computer program code mechanism further comprises:

a patient information data field configured to hold patient-specific information regarding a patient that will receive said mammalian cells, said computer program code mechanism being configured to be updated with new information about said patient during an incubation time of said mammalian cells in said computer-controlled bioreactor portion.

7. The computer program product of claim 1, wherein said computer program code mechanism further comprises:

a biological cell data field configured to hold biological cell information pertaining to said mammalian cells, said computer program code mechanism being configured to be updated with new biological cell information about said mammalian cells during an incubation time of said mammalian cells in said bioreactor protion.

8. The computer program product of claim 1, wherein said computer program code mechanism further comprises:

a time period data field configured to hold timing information regarding a period of time that said mammalian cells are incubated in said bioreactor portion.

9. A a bioreactor system for ex vivo maintenance and growth of mammalian cells, comprising:

a central processing unit;

a transportable cassette, separable from said central processing unit having,
  a data path to said central processing unit;
  a bioreactor having a cell growth chamber and a gas chamber;
  a computer storage medium encoded with a computer code mechanism that when executed by the central processing unit through said data path controls environmental conditions in the bioreactor to be suitable for the ex vivo maintenance and growth of the mammalian cells, said computer storage medium being encoded with,
    a media flow rate parameter embedded therein and being accessible via said data path to said central processing unit when maintaining a predetermined media flow rate through the cell growth chamber so as to maintain the environmental conditions to be suitable for the maintenance and growth of the mammalian cells; and means for monitoring process data while said mammalian cells are maintained and grown in said bioreactor.

10. The bioreactor system of claim 9, further comprising:

means for controlling said predetermined media flow rate using said process data monitored by said means for monitoring.

11. The bioreactor system of claim 9, further comprising:

means for inoculating said bioreactor of said transportable cassette with an initial sample of said mammalian cells.

12. The bioreactor system of claim 9, further comprising:

means for harvesting said mammalian cells from said bioreactor.

13. A computer-controlled bioreactor for ex vivo maintenance and growth of mammalian cells, comprising:

a transportable cassette having
  a cell growth chamber having a media inlet, a media outlet and an internal volume;
  a gas permeable, liquid impervious member disposed within said internal volume so as to divide said internal volume into a gas chamber and a cell growth chamber;
  a computer storage medium encoded with a computer code mechanism that when executed by a processor that is external to said transportable cassette controls environmental conditions suitable for the ex vivo maintenance and growth of the mammalian cells, said computer program code mechanism including,
    a media flow code mechanism having a media flow rate parameter embedded therein and being accessible to said processor when maintaining a predetermined media flow rate through the cell growth chamber by way of said media inlet.

14. The bioreactor of claim 13, wherein said computer program code mechanism further comprises:

a temperature control mechanism configured to maintain a predetermined temperature within said bioreactor.

15. The bioreactor of claim 13, wherein said computer program code mechanism further comprises:

a gas mixture and gas concentration control mechanism configured to control a mixture of gases and a concentration of the mixture of gases in the gas chamber.

16. The computer-controlled bioreactor of claim 13, wherein said computer program code mechanism further comprises:

an inoculation code mechanism configured to control an inoculation operation in said bioreactor with said mammalian cells while maintaining said bioreactor in said mammalian cells in a sterile environment.

17. The computer-controlled bioreactor of claim 13, wherein said computer program code mechanism further comprises:

a harvesting code mechanism configured to control a cell harvesting operation of said mammalian cells from said cell growth chamber while keeping said mammalian cells in a sterile environment.

* * * * *